(12) United States Patent
Fukutomi

(10) Patent No.: US 6,283,121 B1
(45) Date of Patent: Sep. 4, 2001

(54) MANUAL PUMP AND AMBU BAG

(75) Inventor: Osamu Fukutomi, Gifu (JP)

(73) Assignee: Fukutomi Healthscience & Service Co., Gifu (JP)

( * ) Notice: Subject to any disclaimer, the term of this patent is extended or adjusted under 35 U.S.C. 154(b) by 0 days.

(21) Appl. No.: 09/364,765

(22) Filed: Jul. 30, 1999

(30) Foreign Application Priority Data

Aug. 7, 1998 (JP) .................................................. 10-224160

(51) Int. Cl.[7] .................................................. A61M 16/00
(52) U.S. Cl. .................. 128/205.13; 128/205.14; 128/205.15; 128/205.16; 128/205.17; 128/204.28; 128/203.28
(58) Field of Search .................. 128/205.13, 205.14, 128/205.15, 205.16–205.17, 204.28, 203.28; 222/465.1, 466; 417/234, 487

(56) References Cited

U.S. PATENT DOCUMENTS

| | | | |
|---|---|---|---|
| 513,924 | * | 1/1894 | Harnett . |
| 2,428,451 | * | 10/1947 | Emerson ................................. 128/29 |
| 3,461,866 | * | 8/1969 | Ritchie ............................... 128/145.7 |
| 3,939,830 | * | 2/1976 | da Costa ............................. 128/145.7 |
| 4,334,839 | * | 6/1982 | Flagg ..................................... 417/536 |
| 4,934,360 | * | 6/1990 | Heilbron et al. ................. 128/205.16 |
| 5,222,491 | * | 6/1993 | Thomas ............................ 128/205.13 |
| 5,313,938 | * | 5/1994 | Garfield et al. .................. 128/205.16 |
| 5,323,936 | * | 6/1994 | Wolter et al. ......................... 222/401 |
| 5,511,564 | * | 4/1996 | Wilk ...................................... 128/898 |
| 5,540,240 | * | 7/1996 | Bauer .................................... 128/898 |
| 5,588,958 | * | 12/1996 | Cunningham et al. ................... 604/4 |
| 5,628,305 | * | 5/1997 | Melker ............................. 128/202.29 |
| 5,657,751 | * | 8/1997 | Karr, Jr. ........................... 128/205.18 |
| 5,785,700 | * | 7/1998 | Olson ................................... 604/408 |
| 5,787,880 | * | 8/1998 | Swanson et al. ............... 128/202.28 |

* cited by examiner

*Primary Examiner*—Glenn K. Dawson
*Assistant Examiner*—Mital Patel
(74) *Attorney, Agent, or Firm*—Wells, St. John, Roberts, Gregory & Matkin, P.S.

(57) ABSTRACT

An improved manual pump is disclosed. The manual pump comprises a pair of side plates (10), a flexible cylindrical wall (15), a pump chamber (21), an axial shaft (11), a coil spring (12) and a pair of handle bars (16) secured to the side plates (10). When the handle bars (16) are grabbed and clutched with a hand, the side walls (10) are turned in opposite directions, twisting the pump chamber (21) to discharge fluid. The coil spring (12) assists to restore the original shape of the pump chamber (21) to charge fluid.

4 Claims, 2 Drawing Sheets

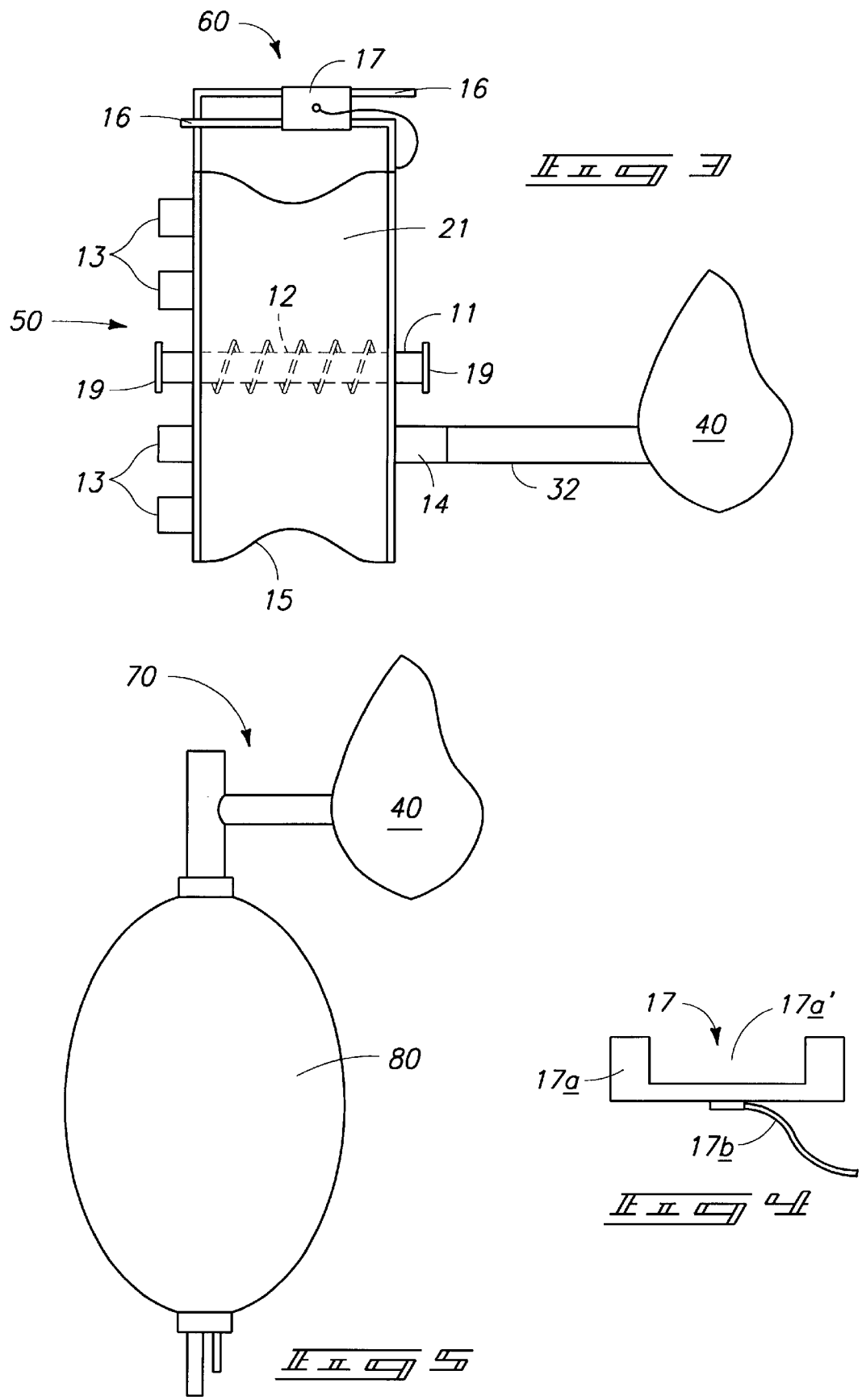

MANUAL PUMP AND AMBU BAG

BACKGROUND OF THE INVENTION

1. Field of the Invention

This invention relates to an improved hand-operated or manual pump for fluid. This invention also relates to an improved Ambu bag which can be operated by a single person for a long time.

2. Prior Art

A popular conventional hand-operated pump comprises a cylindrical bellows body formed of a flexible plastic or rubber material, which may be made thick and resilient so as to assist to restore its expanded or original configuration after the bellows body is manually pressed from both sides with two hands and contracted along its axis to discharge fluid. When the resilience of the bellows body is insufficient, the manual pump requires considerable manual assistance to return to its expanded state to charge fluid. When the resilience of the bellows body is excessive, the manual pump requires its operator to exert considerable energy to contract the bellows body.

Another conventional manual pump utilizes repulsion means such as a coil spring installed within its cylindrical bellows body so that the coil spring may assist the bellows body to restore its expanded configuration after the bellows body is contracted. Such a spring-assisted manual pump is disclosed in Japanese Utility Model Application Laid-Open Publication No. 48-96503, which requires use of both hands of an operator.

Japanese Utility Model Application Laid-Open Publication No. 55-60481 discloses a vacuum packer including a spring-assisted manual pump comprising a curved base having air charge and discharge means and a plastic bellows pump cylinder body. This device also requires use of both hands.

All those manual pumps not only require use of both hands of an operator but also keep occupying both hands, preventing the operator from doing anything else while operating the manual pumps.

When such a pump mechanism is incorporated into an Ambu bag, properly holding a facemask of the Ambu bag on a patient while concurrently activating the Ambu bag is virtually impossible for a single operator since both hands of the operator are kept on the bag. Such an Ambu bag requires at least two persons for a practical medical operation.

Another conventional Ambu bag is shown in FIG. 5, indicated by "70", comprising a rugby ball-like bag or chamber 80 and a facemask device 40 connected to the chamber 80 in fluid communication. The bag 70 is generally made of a "thick" and resilient rubber material to provide quick recovery of shape of the bag after its deformation with a hand or hands. Although it may be possible to activate the pump chamber 80 with a single hand, it is very energy consuming or fatiguing to keep activating or repeatedly squeeze such a thick bag for a long time with a single hand as will be readily understood by medical practitioners. The operator will frequently have to switch hands or use both hands, or another person must take over the operation. Thus, it usually requires at least two medical persons to apply an Ambu bag on a patent for a long time, one squeezing the bag and the other applying a facemask.

SUMMARY OF THE INVENTION

Accordingly, it is an object of the present invention to provide a manual pump which can be easily operated with a single hand with minimum energy.

It is another object of the present invention to provide an Ambu bag incorporation such a manual pump.

It is another object of the present invention to provide such a manual pump or Ambu bag which can be held contracted for compact storage and easy transportation.

Other objects of the present invention will become apparent to people skilled in the art from the descriptions hereunder.

A manual pump of the present invention comprises a pair of side plates arranged a distance apart, generally in parallel, a pump chamber provided between these side plates, an axial shaft provided through the pump chamber, a pair of handle bars arranged a distance apart, generally in parallel, and firmly secured to edge portions of the side plates respectively, and spring means generally provided in and through the pump chamber.

The pair of side plates are preferably circular disks made of a light material such as a rigid plastic or aluminum material. Other materials such as wood may be equally utilized. The diameter and thickness of the side plates can be appropriately selected so as to serve purposes of use. Each side plate may be provided with a center hole of an appropriate size to receive an end portion of the axial shaft airtight.

The pump chamber is a space provided between the side plates, which is enclosed with a flexible cylindrical wall of an appropriate thickness whose round edges are secured airtight to the circumferential edges of the side plates, respectively, with appropriate securing means. The material for the flexible cylindrical wall may be vinyl chloride, polyethylene, nylon, or synthetic or natural rubber. It is advantageous that the cylindrical wall possesses a degree of resilience to assist in restoration of shape. Other flexible materials may be utilized as well.

The axial shaft is generally a round rod. The axial shaft will retain the side plates always in alignment while the side plates relatively rotate about the axial shaft and the distance between the side plates changes. The end portions of the axial shaft may be respectively received in the center holes of the side plates slidably in all directions but held airtight with the center holes with seal means such as O-rings. Alternatively, one of those end portions may be firmly fixed in the corresponding center hole. Still alternatively, an end of the axial shaft may be firmly secured directly on a side plate (having no center hole). In both cases, only the other unfixed end portion of the axial shaft can slide freely relative to the corresponding center hole (while being held airtight). The axial shaft may be made of a rigid plastic material such as hard-type polyethylene, nylon, or polyacetal. Other appropriate rigid materials may be equally used.

The pair of handle bars are firmly secured respectively to edge portions of the side plates, keeping an appropriate distance apart, generally in parallel, such that the handle bars can be comfortably grabbed with a single hand and clutched towards each other. As the handle bars approach each other, the side plates are turned relative to each other about the axial shaft, twisting the flexible cylindrical wall to reduce the volume of the pump chamber, discharging air or liquid from the pump chamber. As the handle bars return to their normal position with assistance from spring means (to be further described later) and possibly from the resilience of the cylindrical wall, the pump chamber restores its normal shape, charging fluid into the pump chamber. Preferably, each handle bar may comprise a bar portion which extends at a right angle with its corresponding side plate towards the other, and in parallel with the cylindrical wall, both bar portions extending in opposite directions.

As described earlier, the spring means assists restoration of shape of the pump chamber. The spring means is preferably a coil spring provided through the pump chamber and around the axial shaft with both ends of the coil spring secured internally to the side plates, respectively. Alternatively, one or both of the ends of the coil spring or spring means may be unsecured.

To function as a pump, it is required to further provide suction or charge means and expelling or discharge means. The charge means and the discharge means are internally provided with one-way valve means. Advantageously, the manual pump of the present invention is provided with a plurality of the charge holes or pipes such that air or liquid may be sucked into the pump chamber efficiently, which assists to promote speed of shape restoration. Alternatively, a single sufficiently large-sized charge hole may suffice. Such charge holes or pipes may be provided on one of the side plates or on both side plates. The discharge means is generally a single hole or pipe provided on one of the side plates.

It is important to note that handle bar clutching operation with a hand according to the present invention is much less fatiguing than bag pressing operation with finger tips, partly thanks to the action of levers, as will be readily appreciated by people in the relevant art.

It is also important to note that shape restoration of a twisted plastic cylindrical wall assisted by spring means according to the present invention is generally far more reliable than that of a plastic bellows bag assisted by spring means or rugby football-like bag, as will be readily appreciated by people in the relevant art.

A flexible plastic or rubber hose having a facemask on one end thereof may be attached to the discharge hole or pipe at the other end of the hose to provide an Ambu bag device. Such an Ambu bag can be operated by a single person easily and without suffering much fatigue. Thus, it is possible for a single medical person to continue to apply the Ambu bag on a patient for a long time without help from another person, which is not possible or at least very hard with a conventional Ambu bag.

Locking means to hold the handle bars together may be additionally provided to hold the manual pump or Ambu bag contracted for compact storage and easy transportation. Stopper means to prevent the axial shaft from slipping off the pump chamber may also be additionally provided.

Other features and advantages of the present invention will be understood from the following detailed description of preferred embodiments of the present invention.

BRIEF DESCRIPTION OF THE DRAWINGS

FIG. 3 is a side elevational view of the Ambu bag of FIG. 1, which is held contracted;

FIG. 4 is an enlarged view of locking means used to hold handle bars together; and FIG. 5 shows a conventional Ambu bag.

DETAILED DESCRIPTION OF PREFERRED EMBODIMENT

Figure 1:
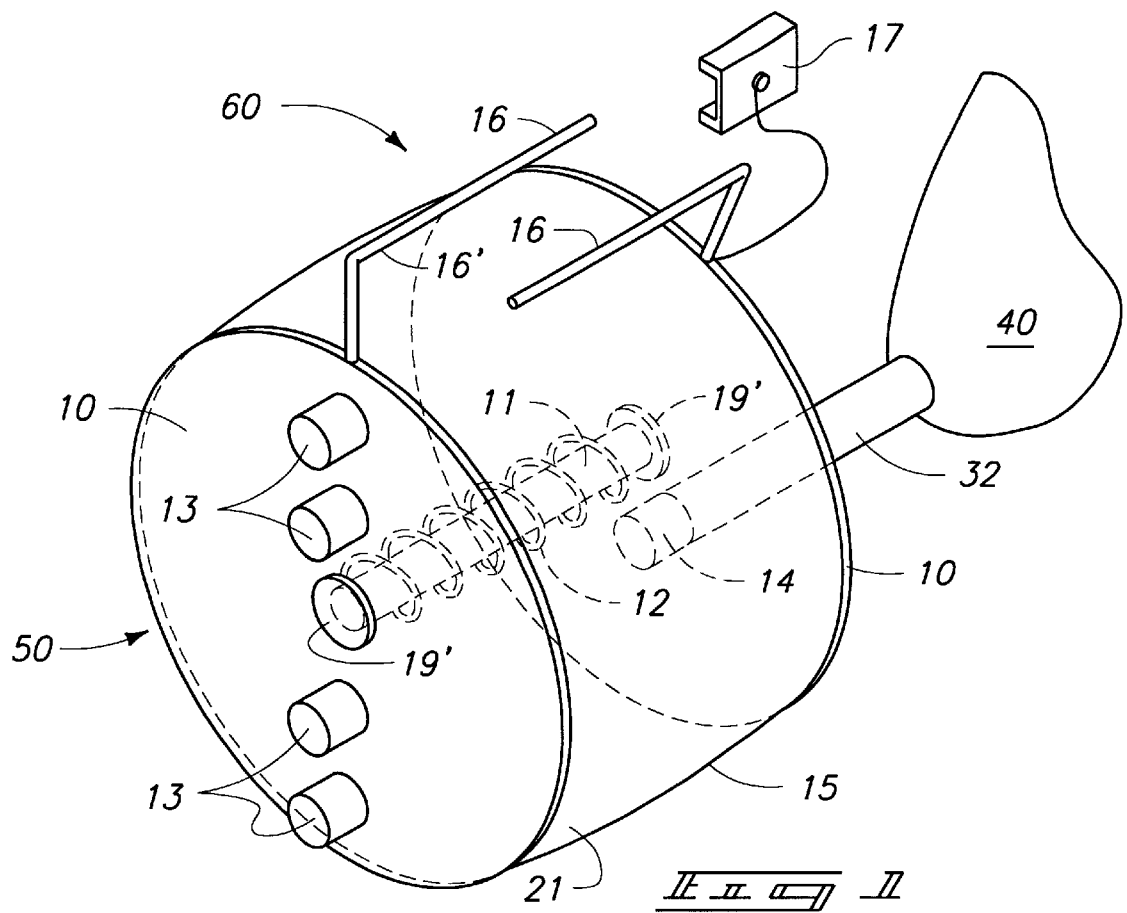
FIG. 1 is a perspective view showing an Ambu bag incorporating a manual pump according to an embodiment of the present invention.
Figure 2:
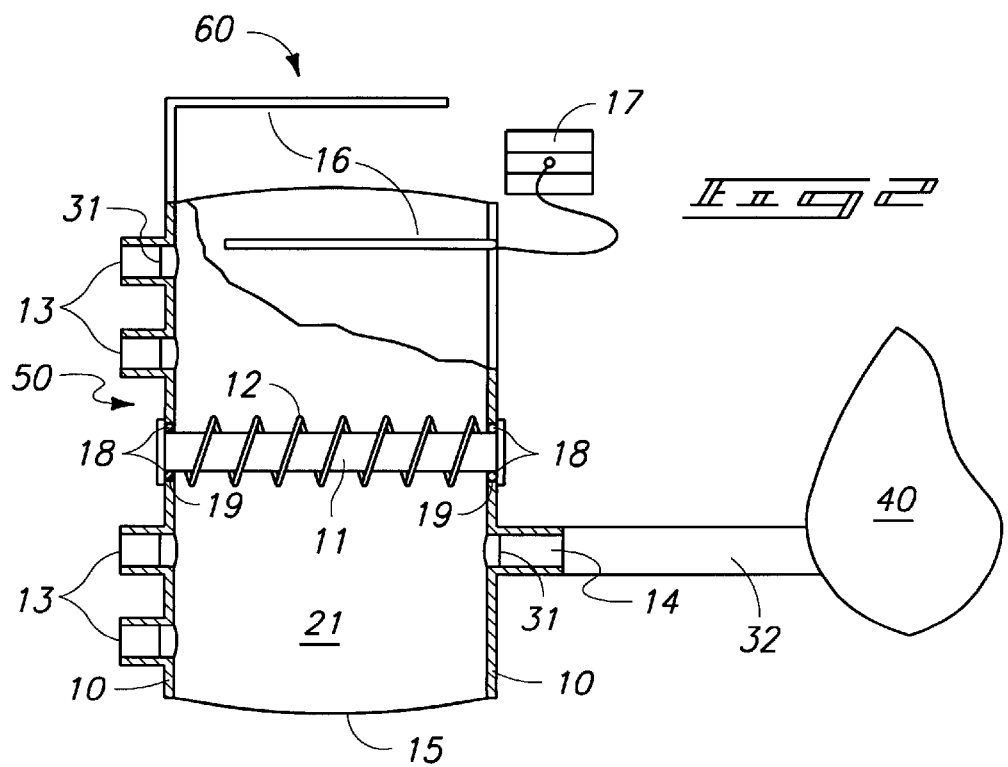
FIG. 2 is a sectional view of the Ambu bag of FIG. 1.

In FIGS. 1 and 2 is shown an Ambu bag 60 according to an embodiment of the present invention, comprising a manual pump 50 of the present invention and a conventional facemask 40 connected to the manual pump 50 with a flexible hose 32.

The manual pump 50 comprises a pair of circular side plates 10 each having a center hole 19 to respectively receive and hold an end portion of an axial shaft 11 slidably but airtight with O-rings 18. The end portions of the axial shaft 11 received respectively in the center holes 19 can freely slide or move relative to the center holes 19 or side plates 10. A coil spring 12 is provided between the side plates 10, through which the axial shaft 11 runs.

A pump chamber 21 is a space enclosed with the side plates 10 and a flexible cylindrical plastic or rubber wall 15 whose edges are respectively secured airtight to the circumferential edges of the side plates 10 with appropriate securing means such as an adhesive.

Four charge pipes 13 each internally having a one-way charge valve 31 are provided in and through one of the side plates 10 to such or charge air into the pump chamber 21. A discharge pipe 14 internally having a one-way discharge valve 31 is provided in and through the other side plate 10, to which a flexible discharge hose 32 is connected. On the outer end of the discharge hose 32 is provided a conventional facemask 40.

A stopper 19' is provided on each end of the axial shaft 11 to prevent accidental slipping off of the axial shaft 11 from the side plates 10.

A pair of handle bars 16 are secured firmly on edge portions of the side plates 10, respectively. The handle bars 16 are arranged such that bar portions 16' of the handle bars 16 extend in opposite directions at a right angle with the side plates 10 towards the other side plates 10. The bar portions 16' are provided generally in parallel with each other and adequately apart so that a single hand (not shown) can grab the bar portions 16' comfortably and easily clutch the bar portions 16' towards each other.

Locking device 17 such as shown in FIG. 4 may be additionally and advantageously provided to hold the handle bars 16 together for compact storage and east transportation of the Ambu bag 60. The locking device 17 in this embodiment is a plate device comprising a locking body 17a having a locking portion 17a' and a string 17b. The bar portions 16' are secured and locked in the locking portion 17a' together, and the string 17b is fixedly secured to an appropriate portion of a side plate 10.

When the handle bars 16 are clutched towards each other with a single hand, the side plates 10 turn about the axial shaft 11 in opposite directions. The flexible cylindrical wall 15 is then twisted to reduce volume of the pump chamber 21 as shown in FIG. 3, which discharges air from the pump chamber 21 through the discharge pipe 14 and the discharge hose 32 into and out of the facemask 40.

Air is sucked into the pump chamber 21 through the charge pipes 13 as the pump chamber 21 increases volume when the handle bars 16 are released and depart from each other into their respective original positions thanks to the coil spring 12 and possibly to the resiliency of the flexible cylindrical wall 15.

In use on a patient, a medical person grabs the bar portions 16' of the handle bars 16 with one hand, and then applies and holds the facemask 40 over the patient's mouth and nose with the other hand. The medical person clutches the bar portions 16' at an appropriate speed and repeatedly at appropriate intervals.

Since that clutching operation can be performed with minimum energy, partly thanks to the act of levers, the medical person can continue this operation for a long time.

It is noted that a manual pump of the present invention can be utilized for a liquid pumping operation as well.

The present invention has been described using embodiments thereof. It is to be understood that various modifications and changes thereto are possible within the scope of the invention. The true scope of the invention is provided by the appended claims.

What is claimed is:

1. A manual pump comprising:

a pair of side plates having discharge and charge mechanisms;

a flexible wall enclosing the side plates to define a pump chamber;

an axial shaft provided between said side plates such that the side plates can turn about said axial shaft, rotation of one of the side plates relative to the other of the side plates changing the volume of the pump chamber to provide for pumping by axial rotation;

handle bars respectively secured to said side plates using which an operator can rotate the side plates relative to one another; and a spring provided between said side plates so as to assist to restore the original shape of said pump chamber after rotation.

2. The manual pump according to claim 1, further comprising a handle bar locking mechanism.

3. The manual pump according to claim 1, wherein the pump chamber has an inlet, and wherein the manual pump further comprises a one way valve in fluid communication with the inlet.

4. The manual pump according to claim 3, wherein the pump chamber has an outlet, and wherein the manual pump further comprises a one way valve in fluid communication with the outlet.

* * * * *

UNITED STATES PATENT AND TRADEMARK OFFICE
CERTIFICATE OF CORRECTION

PATENT NO. : 6,283,121 B1
DATED : September 4, 2001
INVENTOR(S) : Osamu Fukutomi It is certified that error appears in the above-identified patent and that said Letters Patent is hereby corrected as shown below:

<u>Column 4,</u>
Line 39, delete "east"; replace with -- easy --

Signed and Sealed this

Thirtieth Day of April, 2002

Attest:

JAMES E. ROGAN
*Attesting Officer*  *Director of the United States Patent and Trademark Office*